United States Patent
Bauer et al.

[11] Patent Number: 5,971,153
[45] Date of Patent: Oct. 26, 1999

[54] PACKAGE COMPRISING AN ARRAY OF COMPRESSED ABSORBENT ARTICLES

[75] Inventors: Rainer Richard Bernd Bauer, Wiesbaden, Germany; Andre Franz Sturm, Surco Lima, Peru; Georg Pfeifer, Euskirchen, Germany

[73] Assignee: The Proctor & Gamble Company, Cincinnati, Ohio

[21] Appl. No.: 09/091,611

[22] PCT Filed: Dec. 9, 1996

[86] PCT No.: PCT/US96/19487

§ 371 Date: Nov. 13, 1998

§ 102(e) Date: Nov. 13, 1998

[87] PCT Pub. No.: WO97/23391

PCT Pub. Date: Jul. 3, 1997

[30] Foreign Application Priority Data

Dec. 22, 1995 [EP] European Pat. Off. ............. 95120389

[51] Int. Cl.⁶ ................................ B65D 77/00; B65B 5/06
[52] U.S. Cl. ............................. 206/494; 53/438; 53/446; 206/499
[58] Field of Search ................................ 206/494, 497, 206/499, 526; 53/438, 436, 446, 447; 604/258

[56] References Cited

U.S. PATENT DOCUMENTS

| | | | |
|---|---|---|---|
| 2,268,151 | 12/1941 | Huye | 223/71 |
| 3,562,392 | 2/1971 | Mylius | 206/46 |
| 3,645,759 | 2/1972 | Heiligman | 206/499 X |
| 4,934,535 | 6/1990 | Muckenfuhs et al. | 206/494 |
| 5,022,216 | 6/1991 | Muckenfuhs et al. | 53/438 |
| 5,150,561 | 9/1992 | Muckenfuhs et al. | 53/438 X |
| 5,507,130 | 4/1996 | Young et al. | 53/438 |
| 5,642,602 | 7/1997 | Young et al. | 53/438 |
| 5,644,897 | 7/1997 | Young et al. | 53/438 |
| 5,666,787 | 9/1997 | Young et al. | 53/438 |

FOREIGN PATENT DOCUMENTS

| | | | |
|---|---|---|---|
| 0 391 460 | 10/1990 | European Pat. Off. | B65D 83/08 |
| 0 618 148 A1 | 10/1994 | European Pat. Off. | B65D 71/00 |
| 2429908 | 1/1976 | Germany | 53/436 |
| 26 14 235 | 10/1977 | Germany | B65D 85/16 |

*Primary Examiner*—Bryon P. Gehman
*Attorney, Agent, or Firm*—William Scott Andes

[57] ABSTRACT

A package (1) comprising an array (3) of compressed, flexible absorbent articles (5) that have a front face (7), a back face (9), a top face (6), a bottom face (8), side faces (10), an upper section (11) and a lower section (13). The upper and lower sections have mutually different compressibilities and calipers, and the absorbent articles are placed with the front and back faces in a contacting relationship. The package comprises a flexible outer casing (19). The array has a first region (15) and a second region (17) and the upper and lower sections of the absorbent articles are distributed over the first and second regions of the array in such a manner that the difference in the compression force F for compression of the first and second regions to between 20% and 70% of their uncompressed volume is at least 10% smaller than the difference in the compression force for compression of the first and second regions when all of the upper sections of the absorbent articles are located in the same region of the array.

9 Claims, 7 Drawing Sheets

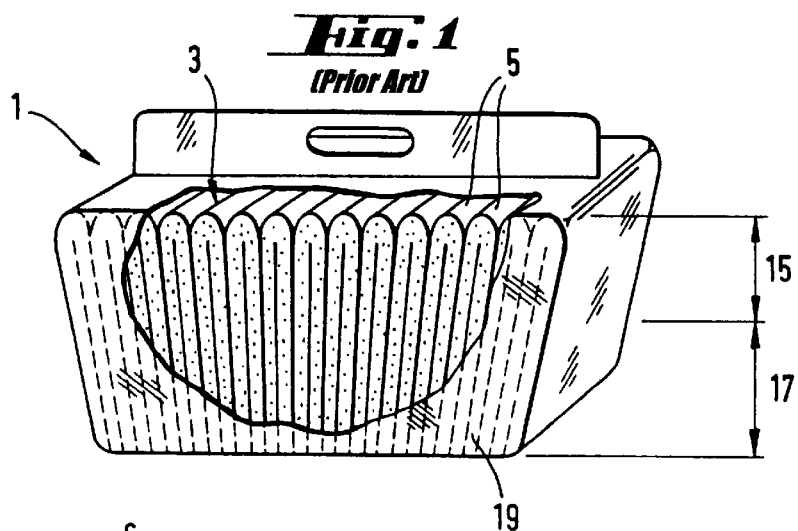
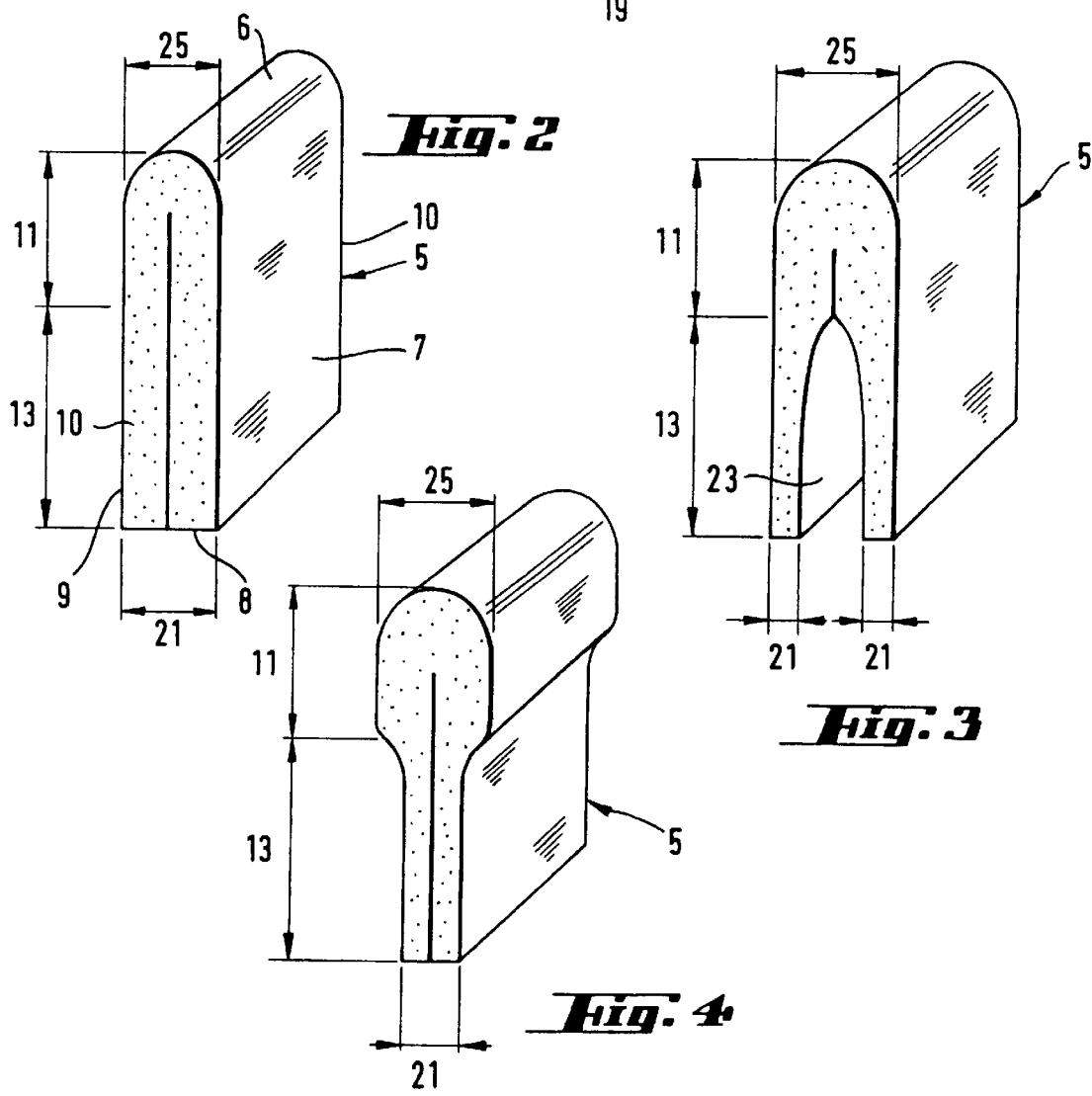

PACKAGE COMPRISING AN ARRAY OF COMPRESSED ABSORBENT ARTICLES

FIELD OF THE INVENTION

The invention relates to a package comprising an array of compressed, flexible absorbent articles, in particular, disposable absorbent articles such as diapers. The package comprises a flexible outer casing and the absorbent articles within are arranged such that their front and back faces are in a contacting relationship. In another aspect of the invention, a method of forming the package is described.

BACKGROUND OF THE INVENTION

It has been recognized that during compression packaging, local variations in compressibilities or calipers can result, which may lead to the flexible outer casing not being filled to an optimal extent. If a high degree of compaction occurs, certain areas of the absorbent articles can be affected, e.g., high compression resistant parts, mechanical fasteners, elasticized internal standup barrier cuffs, waist bands or elasticated side panels, and this can lead to either product damage or to reduced absorption performance.

When flexible disposable absorbent articles are compression packaged, volume changes occur which can lead both to "wedge-like" shapes and to the absorbent articles in the centre of the array being squeezed out. To counteract such an effect, special confinement measures are taken to stabilize the array at its side faces in a direction perpendicular to the direction of compression. As a consequence, the speed of compression packaging is reduced. In addition, the difference in the compressibilities or calipers of parts of the absorbent articles may lead to relatively unstable and easily deformable packages. Therefore, for the purposes of storage of such unstable packages in a shape-stable stack, rectangular load bearing cartons are employed.

From EP-A-0618148 a compressed array of flexible articles is known, which comprises one or more unit packages that are maintained in their compressed state by a paper wrapping. The whole compressed array is encircled in a flexible covering made from a film of thermoplastic material. The application also discloses an alternative type of unit package where the flexible articles are folded and packed in a "head-to-tail" configuration. There is however no suggestion that the compressed state of the array could be maintained even in the alternative configuration without the presence of the individual paper wrappings. Moreover, in order to get access to the products, the consumer has to tear open the outer plastic flexible covering and remove the inner paper wrapping across the width of the products.

In view of the above problems, the present invention seeks to provide a package comprising an array of compressed, flexible absorbent articles that:

o makes efficient use of the available packaging volume by redistributing the orientation of the absorbent articles before compression packaging;

o can be compressed to a relatively small volume without causing damage or a significant reduction in the performance of the absorbent articles;

o reduces the free space inside shipping units (corrugated cases); allows use of ISO modular cases and increases pallet usage;

o is stable with regards to shape (tending towards a rectangular design for a better fit when the package is displayed e.g. on supermarket shelves) and has an improved appearance;

o allows for easier consumer access to the single absorbent articles contained in the flexible outer casing when opened.

o eliminates the need for inner shapes/compression maintaining means such as e. g. paper wrapping The invention further discloses a relatively simple and reliable method for compression packaging of an array of flexible absorbent articles at high speed.

SUMMARY OF INVENTION

The invention describes a package comprising an array of compressed, flexible absorbent articles, which are housed in a flexible outer casing. The array has two regions, namely a first and a second region. The absorbent articles comprise top and bottom faces, front and back faces and side faces that are distributed over the first and second region of the array. For simplicity, the relevant parts of the top, front, back and side faces of the absorbent article are referred to as the upper section and the relevant parts of the bottom, front, back and side faces of the absorbent article are referred to as the lower section. The upper and lower sections have mutually different compressibilities and calipers. The difference in the compression force for compression of the first and second regions (to within 20% to 70% of their uncompressed volume) when the upper and lower sections are distributed throughout the array is at least 10% smaller than the difference in the compression force for compression of both regions when all the upper sections are located in the same region of the array.

By redistributing the orientation of the absorbent articles before compression packaging, the compressibility of the array becomes more uniform. The difference in the degree of compaction of the absorbent articles in the upper and lower sections of the array, in order to obtain an equal reduction in the volume of the first and second regions, is therefore reduced. This prevents over-compression of parts of the absorbent articles, hinders damage to the absorbent articles and improves compression-related performance. In addition, the tendency for the absorbent articles in the centre of the array to be squeezed out is reduced. Hence, more absorbent articles can be compressed in a single array before the array becomes unstable, and the lateral confinement upon compression may be omitted. In this way, the compression process is simplified and an increase in the production speed is achieved. Furthermore, an improvement in the load bearing properties and shape stability of the package occurs. The package of compressed absorbent articles can be stacked in a more stable manner. It has also been found that a package according to the present invention can be compressed by at least 10% more in the direction of compression in comparison to a package comprising an equal number of absorbent articles wherein all the upper sections are located in the same region of the array.

In an embodiment of a package according to the invention, the absorbent articles are distributed in such a manner that the compression forces for the first and second regions of the array are substantially equal. In this way, it is possible to simplify the compression apparatus as the need for a pivoting preventive support for the compression plates to accommodate the different compressibilities of the array can be reduced.

Alternatively, the absorbent articles may be orientated in such a manner that after compression the expansion force of the first region of the array is substantially equal to the expansion force of the second region in order to counteract deformation of the package upon removal of the compression forces.

An array can be formed by stacking bi-folded diapers together, which have either non-uniform calipers or have low and high density regions. As it is well known in the art, a bi-folded diaper is a diaper folded once on itself at its crotch region; such bi-folded diapers have a rounded upper section characterized by a high compression resistance, which corresponds to the crotch region of the unfolded diaper, and a lower section with a low compression resistance, which corresponds to the waist regions of the unfolded diaper. The maximum improvement in compression packaging can be achieved when the orientation of the rounded upper sections is alternated within the array. The orientation however of the upper sections may also be alternated for groups of two or more diapers, and the number of rounded upper sections in the first and second regions of the array of compressed diapers need not necessarily be equal. Tri-folded diapers can also be considered.

The term 'compressibility' is intended to mean the reduction in volume when a predetermined force is applied to an absorbent article or to an array of absorbent articles. This reduction in volume may be between 20% and 70% of the uncompressed volume.

BRIEF DESCRIPTION OF THE DRAWINGS

While this specification concludes with claims particularly pointing out and distinctly claiming the subject matter regarded as the invention, it is believed that a better understanding of the invention can be achieved in conjunction with the study of the attached drawings.

FIG. 1 shows a known package comprising an array of compressed, flexible absorbent articles;

FIGS. 2–4 show a perspective view of folded absorbent articles having upper and lower sections of different compressibilities or calipers;

DETAILED DESCRIPTION OF THE INVENTION

Figure 5:
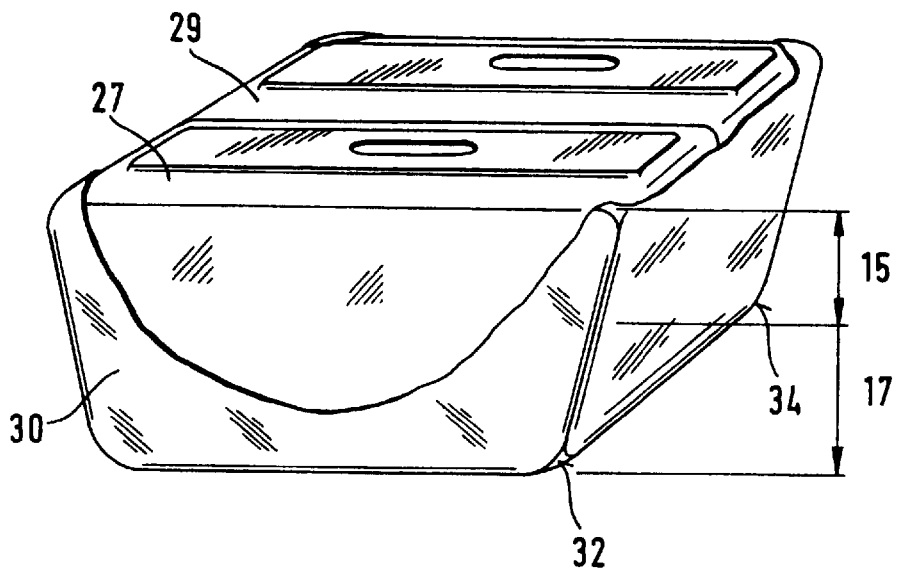
FIG. 5 shows two packages of absorbent articles having deformed corners due to a higher compressibility in the lower region s of the packages.

FIG. 1 shows a package 1 comprising an array 3 of compressed, folded, flexible absorbent articles 5, the array 3 shows a first region 15 and a second region 17. The absorbent articles 5 may comprise diapers, sanitary napkins, incontinence pads or any other type of absorbent article. The absorbent articles 5 are compressed to between 20% and 70% of their uncompressed volume. The absorbent articles 5 are housed in a flexible outer casing 19, with portions of its structure being cut away in FIG. 1 to more clearly show the content of the package. The flexible outer casing 19 maintains the array 3 of compressed articles, and may comprise a thermoplastic bag or a paper bag, as it is known in the art.

Between 10 and 100 absorbent articles 5 are normally comprised in the array 3. As illustrated in FIG. 2, each folded absorbent article 5 comprises a front face 7, a back face 9, a top face 6, a bottom face 8 and side faces 10. In the array 3, the absorbent articles are placed with their front face 7 and back face 9 in a contacting relationship. Each absorbent article 5 comprises an upper section 11 and a lower section 13, as defined in the 'Summary of the Invention' with reference to bi-folded diapers. In the embodiment of FIG. 1, all the upper sections 11 are located in the first region 15 of the array 3. As the first region 15 of the array 3 has a higher compression resistance than the second region 17, the first region 15 of the array will after compression have a larger volume than the lower region 17. This results in a package of non-rectangular dimensions. Furthermore, when a rectangular bag is used for the outer casing 19, the second region 17 of the bag will not be filled to an optimal extent.

FIG. 2 shows a folded absorbent article 5 which is of uniform caliper, i.e., the caliper 25 of the upper section 11 is substantially equal to the caliper 21 of the lower section 13. When different materials are incorporated into the upper section 11 and the lower section 13, mutually different compressibilities result. For example, the upper section 11 may comprise a higher concentration of absorbent gelling material particles or may comprise a resilient liquid acquisition material such as a foamed or a cross-linked cellulose material. Thus, after compression of the absorbent articles 5, the caliper 25 for the upper section 11 and the caliper 21 for the lower section 13 of each article 5 and the dimensions of the first region 15 and the second region 17 of the array 3, along a direction which is orthogonal to the front and back faces 7 and 9 of the absorbent articles 5, will be different.

FIG. 3 shows another embodiment of a folded absorbent article wherein the lower section 13 comprises a gap 23 such that the compressibility of the lower section 13 is increased in comparison to the compressibility of the upper section 11. For many bi-folded diapers, the configuration of FIG. 3 will result as the caliper 25 corresponding to the crotch region of a diaper is generally greater than the caliper 21 corresponding to the waist regions. In the folded absorbent article of FIG. 3, the crotch region forms the upper section 11 and the waist regions form the lower section 13.

In FIG. 4, a folded absorbent article 5 is shown which has a smaller caliper 21 for the lower section 13 in comparison to the caliper 25 of the upper section 11. When the absorbent articles 5 of FIGS. 2–4 are stacked in an array 3, as shown in FIG. 1, and are subsequently compressed, the compression force will be different for the first and second regions 15 and 17 of the array 3. This results in a package 1 of non-rectangular dimensions. Alternatively, the package 1 may have rectangular dimensions that are easily deformable in the second region 17.

FIG. 5 shows a configuration wherein two packages 27 and 29, each similar to package 1, are combined by means of a stretch wrapping film 30. As the compressibility of the first region 15 of the packages 27 and 29 is less than the compressibility of the second region 17, the packages are deformed at their second regions 17. Rounded corners 32 and 34 are formed as the stretch wrap film 30 compresses the lower sections 13 of the absorbent articles 5 located in the second region 17. Therefore, the combined packages 27 and 29 cannot be stacked with other similar packages in a stable manner.

Figure 6:
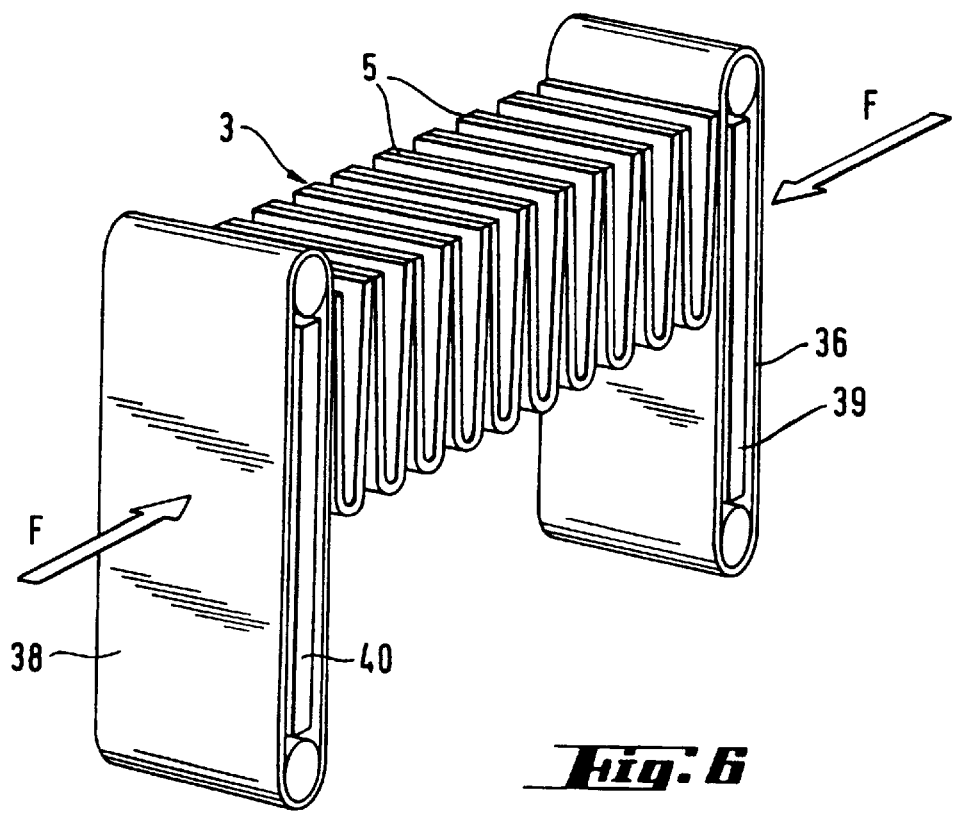
FIGS. 6–8 show a compression packaging apparatus.
Figure 7:
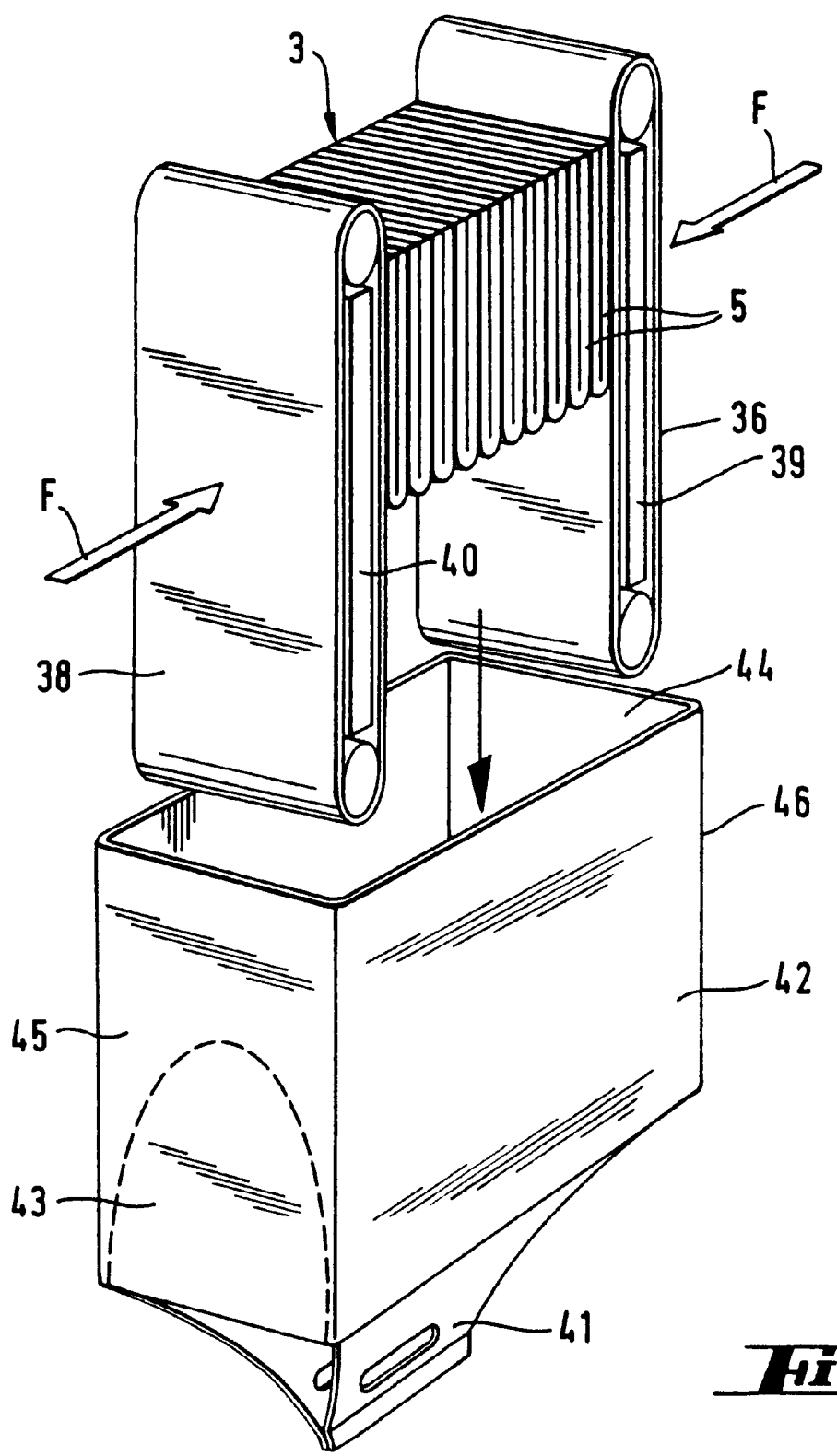

FIG. 6 shows a schematical view of how an array 3 of absorbent articles 5 is compressed between two compression belts 36 and 38. Each compression belt 36 and 38 comprises a compression member 39 and 40, respectively. The array 3 is compressed to between 20% and 70% of its uncompressed volume in the direction of the arrows F by moving the compression members 39 and 40 together with a force that can be as great as 2000 kg. After compression, the belts 36 and 38 are inserted through a bottom surface 44 of a polyethylene bag 42, as shown in FIG. 7. The compressed array 3 is inserted into the bag 42 by rotation of the belts 38 and 36. After the array 3 has been inserted into the bag 42, the belts 36 and 38 are retracted from the bag 42, which is subsequently sealed on the bottom surface 44. (Loading of an array of absorbent articles can also be done using a pusher system.) The bag 42 comprises a handle 41 and an easy opening device 43, which is formed by a line of weakening (perforations) on one of the side surfaces 45 or 46 of the bag 42.

Figure 8:
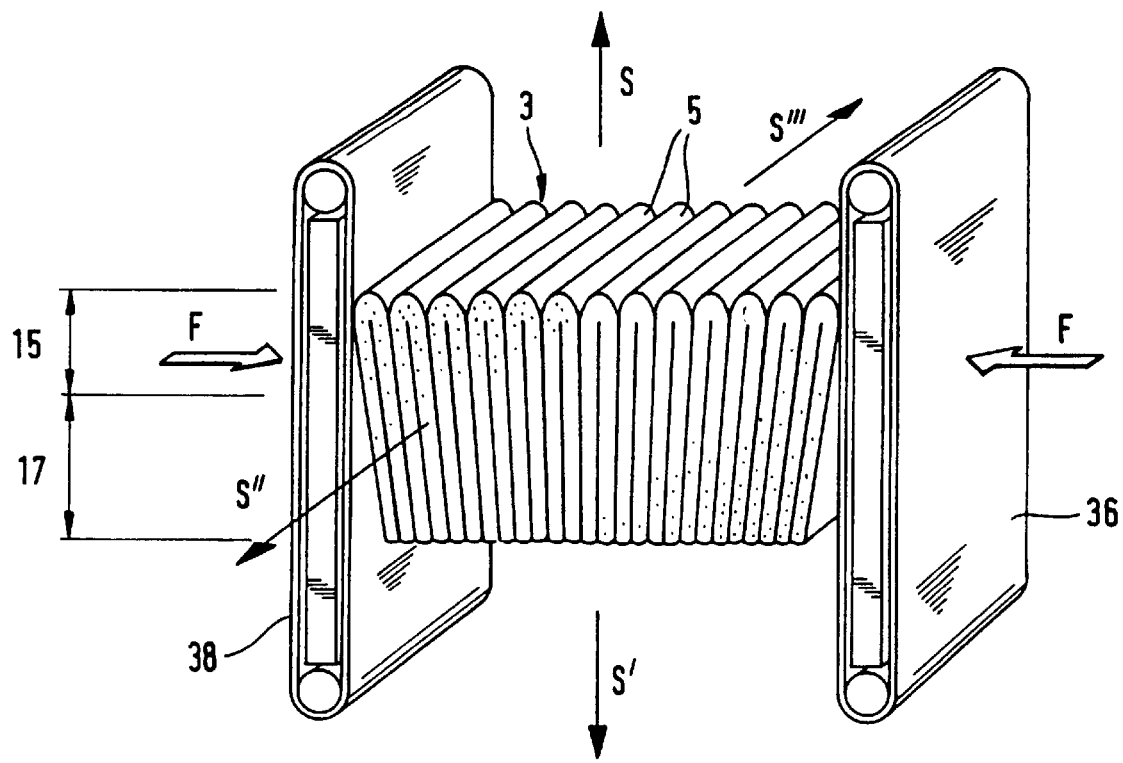

FIG. 8 shows that during compression of the array 3 between the compression belts 36 and 38, each absorbent article 5 is squeezed tightly in the first region 15 of the array 3. This will cause absorbent articles to be squeezed out of the array 3 in the direction of the arrows S or S', S"or S'" depending on the uniformity of the absorbent articles 5. Hence additional compression restraining means are necessary to prevent such a break up of the array 3.

Figure 9:
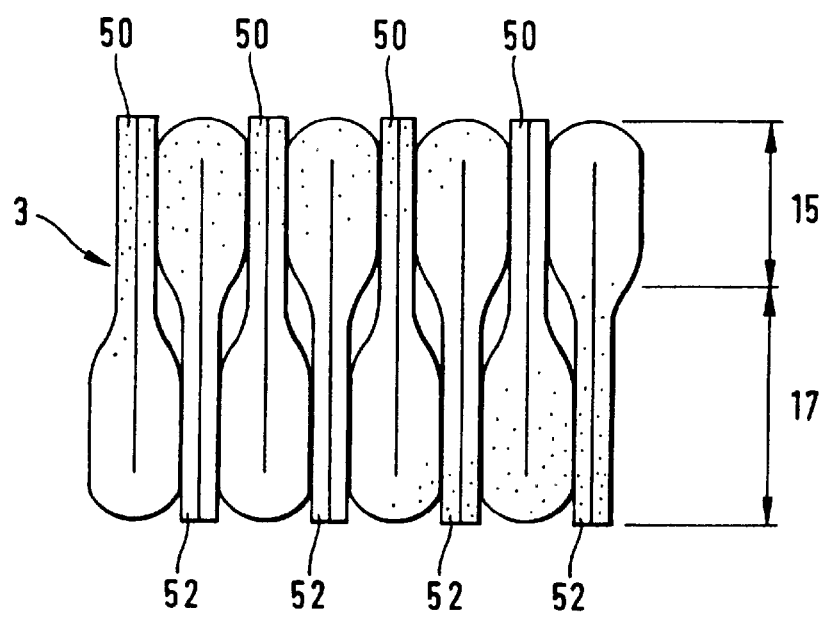
FIGS. 9–12 schematically show arrays of absorbent articles having differently distributed orientations.

FIG. 9 shows the preferred orientation of the absorbent articles 50 and 52 according to the invention. The number of upper and lower sections of the absorbent articles in the first region 15 of the array 3 is either equal to the number of upper and lower sections of the absorbent articles 50 and 52 in the second region 17 of the array 3 or it differs by one. In this way, the compression force necessary to compress the first region 15 is substantially equal to the compression force that is required to compress the second region 17 of the array 3.

Figure 10:
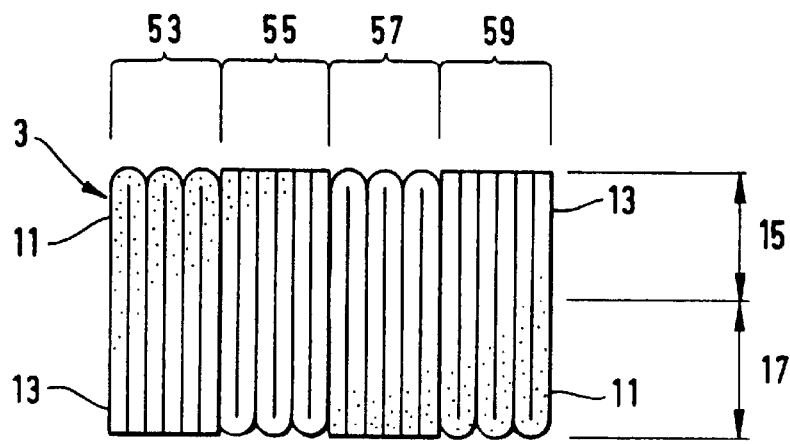
Figure 11:
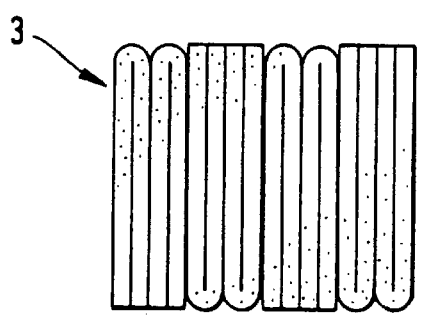
Figure 12:
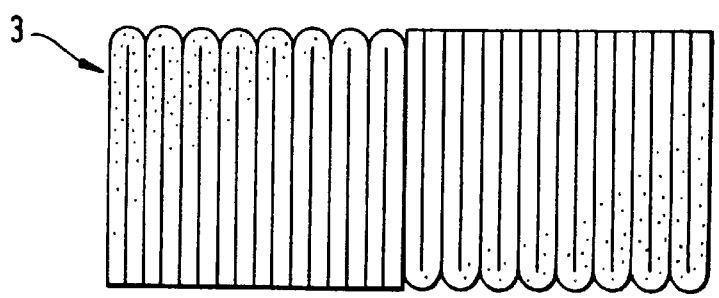

In FIG. 10, the absorbent articles are arranged into groups 53, 55, 57 and 59 such that the upper sections 11 of the absorbent articles in groups 53 and 57 are located in the first region 15 of the array 3 and the upper sections 11 of the absorbent articles in groups 55 and 59 are located in the second region 17 of the array 3. The number of absorbent articles comprised in each group may vary from 2, as illustrated in FIG. 11, to half the number of absorbent articles in the package, as illustrated in FIG. 12. The preferred embodiment occurs when the number of groups are equal to each other, each group comprising a predetermined equal number of absorbent articles.

Figure 13:
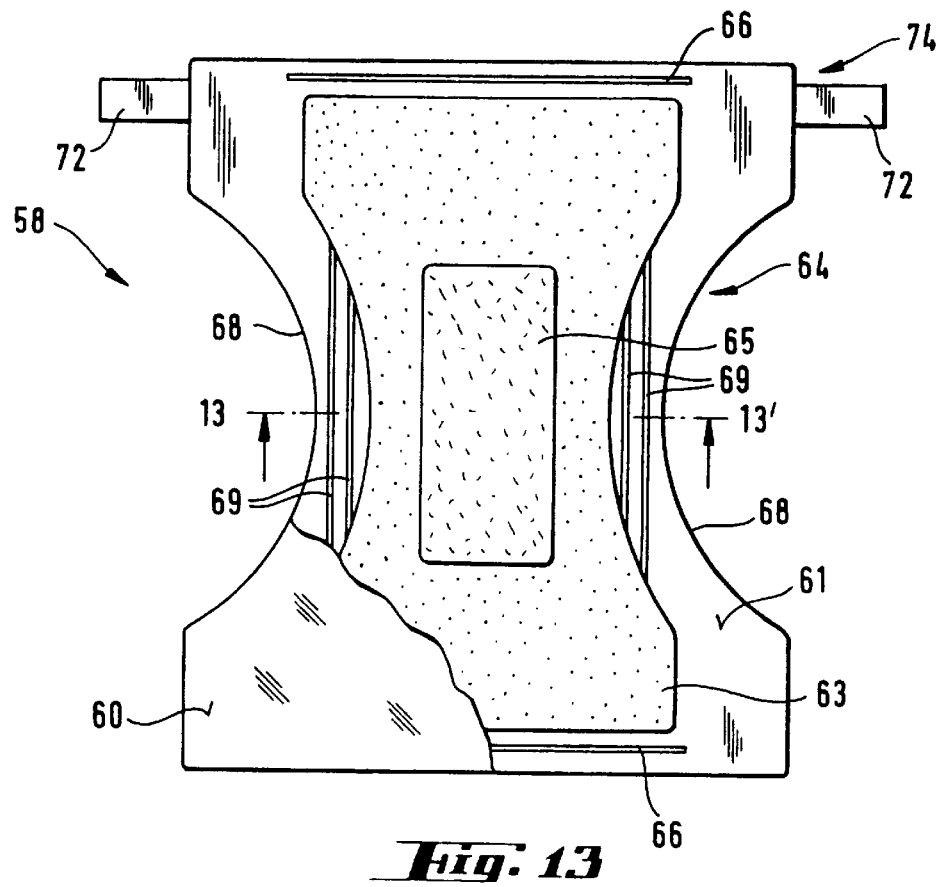
FIG. 13 shows a plan view of a disposable diaper in the flattened state.

FIG. 13 shows a plan view of a flattened disposable diaper 58. The diaper 58 comprises a liquid pervious topsheet 60 and a liquid impervious backsheet 61. In FIG. 13, the topsheet 60 has been largely cut away to show the underlying features. The diaper 58 comprises an absorbent core 63, which may comprise cellulosic fibres and hydrogel forming particles. A central acquisition patch 65 is placed in the crotch region 64 of the absorbent core 63. Leg elastic elements 69 are located in the leg regions 68 of the diaper 58. Front and back waist elastics 66 may be comprised in the diaper 58. A fastening system, which comprises adhesive tape fasteners 72, is connected to the back region 74 of the diaper 58. The fastening system may alternatively comprise mechanical fasteners or a combination of adhesive and mechanical fasteners.

Figure 14:
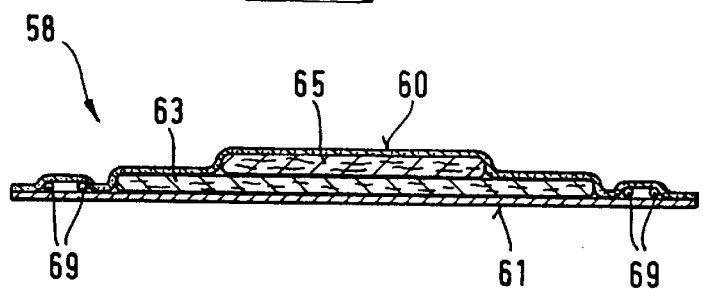
FIG. 14 shows a cross-sectional view of the diaper taken from the view line 13–13' in FIG. 13.

FIG. 14 shows a cross-section of the diaper 58 taken from the view line 13–13' in FIG. 13. On folding the diaper along the line 13–13', the central region of the diaper 58, comprising the acquisition patch 65, will have the highest caliper.

Figure 15:
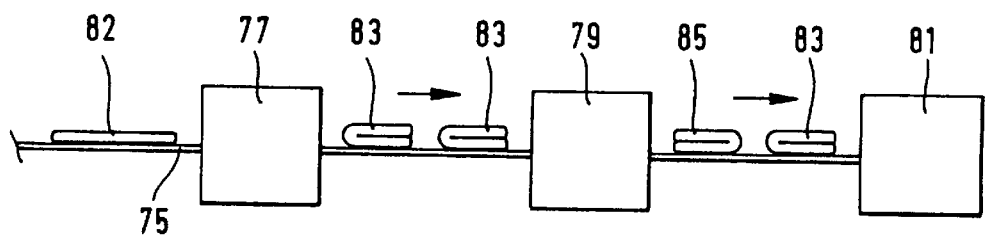
FIG. 15 shows a schematic view of a process for the compression packaging of disposable diapers.

FIG. 15 shows a schematic view of a method for compression packaging of diapers according to the invention. The unfolded diapers 82 are transported on a conveyor belt 75 towards a folding unit 77. In the folding unit, the diapers 82 are doubled over with the aid of, for example, a folding board. The bi-folded diapers 83 are transported from the folding unit 77 to a positioning unit 79. In the positioning unit 79, the orientation of the diapers 83 is altered at pre-determined intervals. The diapers, 85 and 83, are thereafter transported to a compression unit 81 wherein the diapers 85 and 83 are stacked in an array and compressed. The diapers 83 and 85 are then placed in an outer casing, for example, a bag by means of the apparatus shown in FIGS. 6 and 7.

Figure 16:
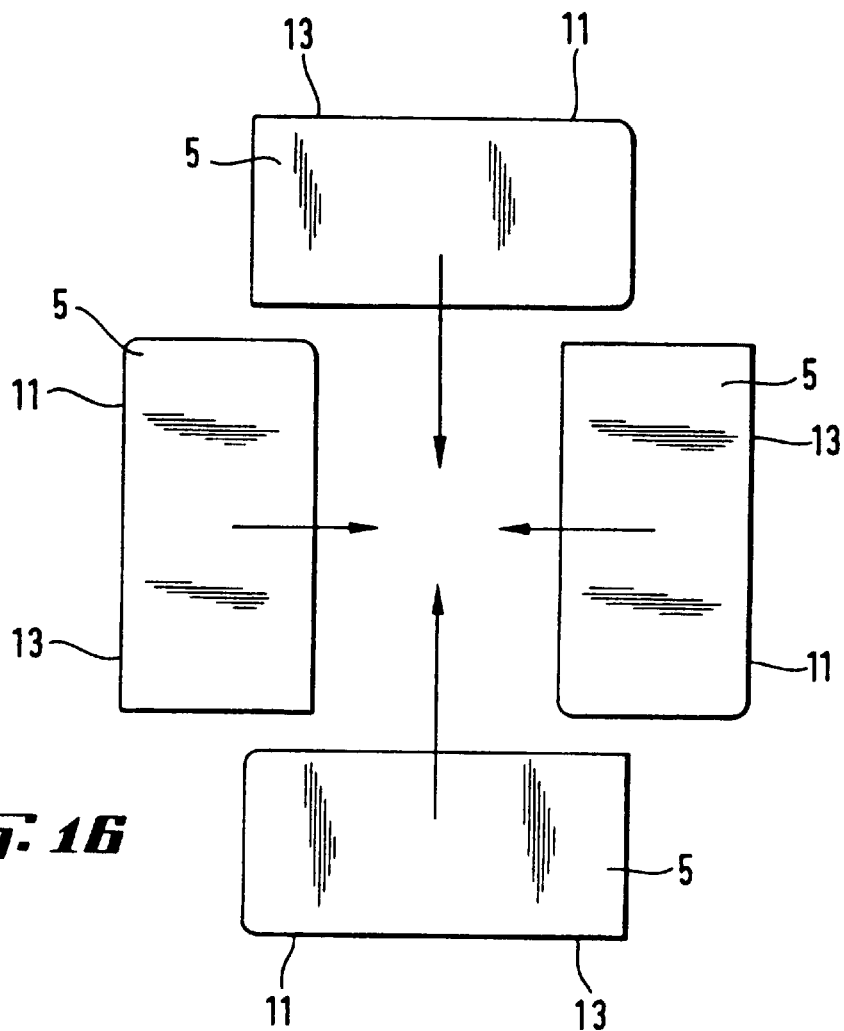
FIGS. 16 and 17 show a different configuration of an array of reabsorbent articles.
Figure 17:
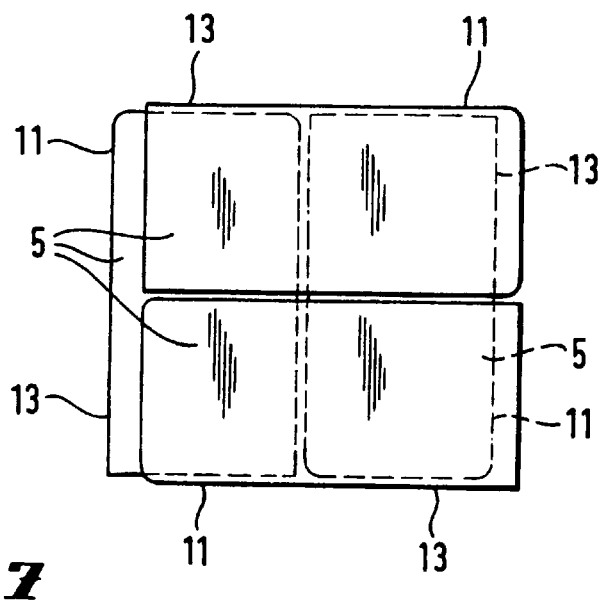

FIGS. 16 and 17 show a schematic view of four absorbent articles 5 whose upper and lower sections 11 and 13 are arranged in an overlapping relationship such that a uniform caliper configuration is formed. For two absorbent articles 5, which are orientated such that they mutually differ by 90°, the upper section 11 overlaps with the lower section 13. An array 3 may thus be formed by stacking several configurations.

What is claimed is:

1. A package (1) comprising an array (3) of compressed, flexible absorbent articles (5), said absorbent articles (5) comprising a front face (7), a back face (9), a top face (6), a bottom face (8), side faces (10), an upper section (11) and a lower section (13), said sections having mutually different compressibilities and calipers, wherein said absorbent articles are placed with said front and back faces (7, 9) in a contacting relationship, said package (1) comprising a flexible outer casing (19), said array (3) having a first region (15) and a second region (17) and said upper and lower sections (11, 13) of said absorbent articles (5) being distributed over said first and second regions (15, 17) of said array (3), wherein said distribution of upper and lower sections (11, 13) is such that the difference in the compression force F for compression of said first and second regions (15, 17) to between 20% and 70% of their uncompressed volume, is at least 10% smaller than the difference in the compression force for compression of said first and second regions (15, 17) when all of said upper sections (11) of said absorbent articles (5) are located in the same region of said array (3); and said flexible outer casing (19) maintains said array (3) of compressed articles.

2. A package according to claim 1, wherein the upper and lower sections (11, 13) of the absorbent articles (5) are distributed in such a way that the compression forces for said first and second regions (15, 17) of the array (3) are substantially equal.

3. A package according to claim 1, wherein the orientation of the absorbent articles is altered at intervals.

4. A package according to claim 1, wherein after compression the dimension along the direction of compression of the first region of the array is substantially equal to the dimension along the direction of compression of the second region of the array.

5. A package according to claim 1, wherein after compression the expansion force of the first region is substantially equal to the expansion force of the second region.

6. A package according to claim 1, wherein said absorbent articles comprise different calipers in the upper and lower sections.

7. A package according to claim 1, wherein said package does not comprise on inner means; to maintain said array of compressed articles.

8. method of forming a package comprising an array of compressed, flexible absorbent articles, said absorbent articles comprising a front face, a back face, a top face, a bottom face, side faces, an upper section and a lower section, said sections having mutually different compressibilities and calipers, wherein said absorbent articles are placed with said front and back faces in a contacting relationship, said package comprising a flexible outer casing, said array having a first region and a second region and said upper and lower sections of said absorbent articles being distributed over said first and second regions of said array, said distribution of upper and lower sections being such that the difference in the compression force F for compression of said first and second regions to between 20% and 70% of their uncompressed volume, is at least 10% smaller than the difference in the compression force for compression of said first and second regions when all of said upper sections of said absorbent articles are located in the same region of said array; and said flexible outer casing maintaining said array of compressed articles; said method comprising the following steps:

transporting said absorbent articles in a consecutive manner to a folding unit, folding said absorbent articles, changing the orientation of said absorbent articles at regularly spaced intervals, aligning a predetermined number of said absorbent articles with said front and back faces in a contacting relationship to form an uncompressed array, wherein a predetermined number of said absorbent articles have their said upper sections located in a first region of said array and a second predetermined number of said absorbent articles have their said upper sections located in a second region of said array, compressing said array, and placing the compressed array in a flexible outer casing.

9. A method according to claim 8, wherein the compression force F is substantially uniform across said first and second regions.

* * * * *

UNITED STATES PATENT AND TRADEMARK OFFICE
CERTIFICATE OF CORRECTION

PATENT NO. : 5,971,153
DATED : October 26, 1999
INVENTOR(S) : Rainer Richard Bernd Bauer et al.

It is certified that error appears in the above-identified patent and that said Letters Patent is hereby corrected as shown below:

Claim 7,
Line 64, please delete "on" and insert therefore -- an --.

Claim 8,
Line 66, please insert -- A -- before the word method.

Signed and Sealed this

Sixth Day of November, 2001

Attest:

NICHOLAS P. GODICI
Attesting Officer    Acting Director of the United States Patent and Trademark Office